United States Patent [19]

Morita et al.

[11] Patent Number: 5,902,908
[45] Date of Patent: May 11, 1999

[54] METHOD FOR PREPARING FLUORINATED VINYL ETHER

[75] Inventors: Shigeru Morita; Yasuji Iwasaki, both of Settsu, Japan

[73] Assignee: Daikin Industries Ltd., Osaka, Japan

[21] Appl. No.: 08/967,731

[22] Filed: Nov. 12, 1997

Related U.S. Application Data

[63] Continuation of application No. 08/360,788, filed as application No. PCT/JP93/00657, May 17, 1993, abandoned.

[30] Foreign Application Priority Data

Jun. 26, 1992 [JP] Japan .................................. 4-193104

[51] Int. Cl.$^6$ .................................................. C07C 43/17
[52] U.S. Cl. ........................... 568/615; 568/614; 568/674
[58] Field of Search .................................. 568/615, 614, 568/674

[56] References Cited

U.S. PATENT DOCUMENTS

| | | | |
|---|---|---|---|
| 3,291,843 | 12/1966 | Fritz et al. .............................. | 260/614 |
| 3,326,984 | 6/1967 | Anderson et al. ....................... | 260/614 |
| 3,351,619 | 11/1967 | Warnell ................................. | 260/80.76 |
| 4,209,635 | 6/1980 | Munekata et al. ....................... | 560/183 |
| 4,420,638 | 12/1983 | Uschold ................................. | 568/415 |
| 4,772,756 | 9/1988 | Bornengo et al. ....................... | 568/684 |
| 5,001,278 | 3/1991 | Oka et al. .............................. | 568/615 |

OTHER PUBLICATIONS

Fearn et al., "Polymers and Telomers of Perfluoro–1,4–Pentadiene", Journal of Polymer Science Part A–1, vol. 4, pp. 131–139, 1966, 1996.

*Primary Examiner*—Dwayne C. Jones
*Attorney, Agent, or Firm*—Armstrong, Westerman, Hattori, McLeland & Naughton

[57] ABSTRACT

The present inventions provide methods to produce fluorinated vinyl ether by reacting fluorinated carboxylic acid halogenide with a metal compound below the decomposition temperature for the corresponding metal salt in the absence of solvent and then raising the temperature of the produced corresponding metal salt above the decompostion temperature. With these production methods, fluorinated vinyl ether of a high purity can be obtained on an efficient basis.

4 Claims, No Drawings

METHOD FOR PREPARING FLUORINATED VINYL ETHER

This application is a continuation of application Ser. No. 08/360,788 filed Dec. 23, 1994, now abandoned, which was a 371 of PCT/JP93/00657 filed May 17, 1993.

FIELD OF THE INVENTIONS

The present inventions relate to production methods of fluorinated vinyl ether, which is industrially useful for fluorine-containing synthetic resin or rubber etc.

PRIOR ART

Fluorinated vinyl ether is known as a raw material that is copolymerized with tetrafluoroethylene (TFE) or other copolymerizable monomers into industrially useful resin and rubber (e.g. PFA resin, which is a copolymer with TFE, perfluoro rubber, denatured PTFE, and synthetic rubbers which are copolymers with other monomers). It is known that fluorinated vinyl ether is obtained by the method contained in Provisional Publication No. 132851/63 and so on.

For example, it is known that fluorinated vinyl ether is obtained through the thermal decomposition of Na salt, which is produced by reacting NaOH and fluorinated ether carboxylic acid fluoride as a raw material. The fluorinated ether carboxylic acid fluoride is produced by polymerizing HFPO (hexafluoropropylene oxide) by means of a catalyst such as CsF in a solvent such as tetraglyme.

There have been various conditions for HFPO polymerization considered. There have also been various processes considered for obtaining vinyl ether from the resulted fluorinated ether carboxylic acid fluoride.

For example, a literature (actually, U.S. Pat. No. 3,132,123) claims that the objective fluorinated vinyl ether is effectively obtained by flowing fluorinated carboxylic acid fluoride (normally in the gaseous state with inert gas as a carrier, such as $N_2$) through a tower filled with a metal oxide or a metal salt and heated at about 300° C. In this reaction, however, temperature control is difficult. As a result, the reaction cannot effectively produce the objective substance of a high purity or at a high yield because this process tends to create unfavorable impurities. The reason for this impurity is thought to be that a local temperature rise at the reaction location causes unfavorable decomposition and the produced carbides cover the surface of the metal compounds, which lowers the reaction rate. This method must, therefore, involve the washing process including rinsing after the reaction and before the rectification. It also encompasses the difficult works of filling metallic compounds into the reaction tube and removing reaction residuals.

Another literature (Provisional Publication No. 132851/63) claims that the objective fluorinated vinyl ether is obtained at a relatively low temperature (the room temperature to 100° C.) by reacting with an alkali such as sodium carbonate in a solvent such as tetraglyme. This process, however, produces a large amount of unfavorable by-products (hydrogen fluoride adducts of fluorinated vinyl ether) because of water contained in the solvent tetraglyme or sodium carbonate. Moreover, the solvent after the reaction contains a suspension of produced fluorinated sodium and other substances so that its repeated use is limited and it is finally disposed as an organic waste liquid. This is not preferable for resource saving and environmental protection.

Another known method of producing the objective fluorinated vinyl ether is that fluorinated carboxylic acid fluoride is neutralized with NaOH etc. and the salt resulted from that reaction is dried and heated above its thermal decomposition temperature. However, drying the salt in this process is considerably difficult, and conditions for the drying are different according to the kinds of fluorinated carboxylic acids. If the salt is not sufficiently dried, the abovementioned unfavorable by-products are produced.

To avoid the production of such by-products, the following process can be used: first reacting fluorinated carboxylic acid with methanol into fluorinated carboxylic acid methylester; distilling the resulted substance to raise its purity and remove water; reacting the distilled substance with NaOH dissolved in methanol; and drying the resulted substance. This method facilitates the drying process and reduces the unfavorable by-products produced. However, this process is longer than the others. It also increases a risk of fire because it uses alcohol. The additional risk requires additional anti-fire measures in equipment.

OBJECT OF THE INVENTIONS

The object of the present inventions is to eliminate the above-stated shortcomings of the prior art and provide an efficient production method of fluorinated vinyl ether of a high purity.

CONSTITUENTS OF THE INVENTIONS

The present inventions relate to a production method of fluorinated vinyl ether through the following process: first reacting an acid halogenide represented by the following general formula I:

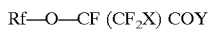
Rf—O—CF (CF$_2$X) COY

{In the general formula, Rf: Rf'—(OCF(CF$_2$X)CF$_2$)$_l$— or Rf'—(OCXYCF$_2$CF$_2$)$_m$—(Rf' is a perfluoroalkyl group with 1 to 4 carbon atoms or CX'Y'Z' (CF$_2$)$_n$—, where X' and Y' are hydrogen atoms, fluorine atoms, chlorine atoms or bromine atoms; Z' is a hydrogen atom, a fluorine atom, a chlorine atom, a bromine atom or an iodine atom; and n=0 to 4. X and Y are fluorine atoms, chlorine atoms, bromine atoms or iodine atoms; l=1 to 4; and m=1 to 4.); X and Y: the same as defined above.} and a metal salt or metal oxide represented by the following general formula II:

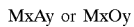
MxAy or MxOy (In the general formula, M: a metal atom; A: a part of carbonic acid or sulfuric acid; O: oxygen atom; x: the valence of A or O; and y: the valence of M)

at a temperature below the decomposition temperature for the fluorinated carboxylic acid metal salt represented by the following general formula III:

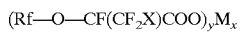
(Rf—O—CF(CF$_2$X)COO)$_y$M$_x$ (In the general formula, Rf, X, M, x, and y are the same as mentioned above)

in the absense of a solvent; and decomposing the fluorinated carboxylic acid metal salt produced by the above-mentioned reaction by raising its temperature above its decomposition temperature to produce the fluorinated vinyl ether represented by the general formula IV:

Rf—O–CF=CF$_2$ (In the general formula, Rf is the same as mentioned above).

The purpose of the present inventions is to efficiently obtain fluorinated vinyl ether of a high purity by reacting an acid halogenide such as fluorinated carboxylic acid halogenide (that may be referred to as fluorinated carboxylic acid fluoride, hereinafter) with a metal compound at a temperature below the decomposition temperature for the corresponding metal salt to the acid halogenide; and then heating the resulted corresponding metal salt above its decomposition temperature.

This process to obtain fluorinated vinyl ether includes the reaction to produce the corresponding metal salt of fluorinated carboxylic acid in the little water environment. If a solvent (a polar solvent in most cases) is used, removing water from the solvent is a problem. If the reaction is directly carried out at a temperature above the decomposition temperature for the metal salt to avoid the problem arising from the use of a solvent, it is accompanied by an unfavorable decomposition as mentioned already so that the yield and purity of the objective substance are low.

However, distilled fluorinated carboxylic acid fluoride as a raw material does not contain water in principle and compounds such as pottasium carbonate can easily be dried by heat (maybe with a carrier gas or under a reduced pressure). With these facts, the inventors have studied the process of producing vinyl ether only with those materials. As a consequence, they have found that fluorinated carboxylic acid fluoride can be easily reacted with metal salts such as potassium carbonate at about 100° C. in no solvent to produce the corresponding metal salt of fluorinated carboxylic acid.

That is, the inventors have found that fluorinated carboxylic acid salt containing virtually no water is obtained directly from distilled acid fluoride and potassium carbonate dehydrated by heat. This discovery amazed them because there had been no report of acid fluoride being reacted as easily as in the discovered process. Furthermore, they were also amazed by the discovery that the reaction occurred on a certain quantitative basis below the decomposition temperature for the metal salt to be produced.

Those substances react well in the still standing condition. (It is assumed that first the reaction occurs on the surface of the solid materials and then progresses with dissolution of produced metal salt by acid fluoride that has not yet reacted. In the case of carbonates used as a material, it is considered that the carbonate produces carbonic acid gas in the reaction, which accelerates the reaction of the solid materials.) It is, however, obvious that stirring still better progresses the reaction. While there may be various ways of stirring, the stirring method should be decided, taking into consideration the followings: solid material being dried before the reaction for the efficiency; the properties of the produced metal salt (e.g. with or without viscosity); and the temperature of the produced metal salt being raised at the decomposition level, for example, if the thermal decomposition process is used as it is.

It is preferable that the mols of acid fluoride and metal salt are equal in the reaction, but it is better to use more mols of metal salt than acid fluoride by nature of the reaction. If the mols of metal salt is fewer than those of acid fluoride, there is some amount of acid fluoride that will not react, so that the yield and purity of the objective substance are low. There is no problem arising from a larger amount of metal salt than acid fluoride. With an amount of metal salt doubling that of acid fluoride, two successive rounds of the entire reaction process can actually be caused without adding the metal salt.

The reaction pressure can be a depressurized pressure or a pressurized pressure but is limited by the boiling point of an acid fluoride used. Acid fluorides with high boiling points can sufficiently react in the atmospheric pressure, while the ones with low boiling points may need to be pressurized to maintain the appropriate reaction temperature. The third substance that does not involve in the reaction can be present together with the materials. However, in such a case, the water content of the third substance must be taken into consideration.

For acid halogenides contained in the above general formula (I) of the present inventions, Rf' may be perfluorides of alkyl groups of methyl, ethyl, propyl, or butyl. However, useful acid halogenides for the reaction include HFPO oligomer $(CF_3CF_2CF_2O(CF(CF_3)CF_2O)nCF(CF_3)COF: n=0$ to 4, shortened as HFPOn), as well as $CF_3CF_2CF_2O-(CF_2CF_2CF_2O)nCF(CF_3)COF:n=0$ to 4 and $CH_3CF_2CF_2O-(CF(CF_3)CF_2O)nCF(CF_3)COF:n=1$ to 2.

Metal salts or metal oxides contained in the above general formula II of the present inventions may be carbonates of alkaline metals and alkaline earth metals (e.g. sodium carbonate and potassium carbonate), sulfates of the metals (e.g. sodium sulfate and potassium sulfate), and oxides of the metals (e.g. magnesium oxide and calcium oxide).

The metal salts produced through the above-mentioned reaction can be heated at the thermal decomposition temperature in the same device as that for the reaction or in another reaction device to produce the objective vinyl ether of a high purity at a high yield without difficulty. The thermal decomposition temperature is determined by that of the salt to be produced. If that temperature is high, there is unfavorable decomposition accompanying the reaction. Accordingly the temperature is preferably 300° C. or lower, or particularly preferably 180° C. to 280° C. For this reason, K salt or Na salt or the like is particularly preferable.

There are no particular restrictions on the pressure for the thermal decomposition. However, reduced pressure is preferable because the products can be distilled into vapor in the atmosphere. It is possible that, after the reaction was made in the atmosphere or a pressurized atmosphere or under reduced pressure the products are distilled or separated through the filtration.

Fluorinated carboxylic acid fluoride tends to be accompanied by the impurities with boiling points in proximity to its own boiling point, which is also close to that of the corresponding vinyl ether. Therefore, those impurities tend to be retained by the objective vinyl ether through the reaction processes. However, those impurities can be easily distilled out under a reduced pressure after the metal salt was produced. This is an advantage of these inventions. Although a little water contained in the materials causes producing a very small amount of hydrogen fluoride adduct of the product, this reaction is seen only at the initial stage of the thermal decomposition reaction. Accordingly, if the products at the initial stage of the thermal decomposition are distilled out, the subsequently produced vinyl ether does not virtually contain hydrogen fluorides adduct.

That is, vinyl ether of an amazingly high purity is obtained through the following process: first fluorinated carboxylic acid fluoride corresponding to the targeted vinyl ether is purified through the distillation process, (which is an essential process for the materials produced through polymerization (oligomerization) because they have a distributive characteristic); that material is reacted with a metal salt dehydrated in advance at 50° C. to 200° C., preferably 90° C. to 180° C., or more preferably 100° C. to 150° C.; the constituents that have not reacted are then distilled out under a reduced pressure, and the initial distillates at thermal decomposition are also distilled out by gradually raising temperature so that the impurities originally contained in the materials and the hydrogen fluoride adduct of the objective product are virtually completely removed, and the thermal decomposition is continued. The obtained vinyl ether can be used for polymerization without need of rinsing, alkali washing or other specific washing processes after only rectification.

The by-products of the above-stated process are only carbonic acid gas and metal fluorides such as potassium fluoride, as well as very small amounts of impurities. Carbonic acid gas is distilled out in the gaseous state to be removed with the alkali removing equipment. Metal fluorides, particularly potassium fluoride etc. can be reused as resources.

The present inventions are thus supposed to be superior to the prior art in all the concerned aspects.

Industrial Applicability

In accordance with the present inventions, fluorinated vinyl ether of a high purity can be efficiently obtained by reacting liquid or gaseous fluorinated carboxylic acid halogenide with a metal compound below the decomposition temperature for the corresponding metal salt to produce that metal salt; and then raising the temperature above that decomposition level.

EMBODIMENTS

Embodiments of the present inventions are shown below, but they shall not be construed as placing any restrictions on the inventions.

Embodiment 1

15 g of potassium carbonate anhydride was put into a flask with a content volume of 100 ml with a reflux cooling device. The substance was dried by heating it in an oil bath at 200° C., being permeated with $N_2$ gas. After it was cooled down below 100° C., 60 g of $HFPO_2$ obtained from the oligomerization of hexafluoropropyleneoxide (HFPO) was quickly dropped in the substance.

When the temperature of the flask content in the oil bath was gradually raised, an intense reaction was occurring with gas produced at about 100° C. The content substances that had initially been a liquid and a white powder changed into white greasy substance. The substance continued to be heated after that reaction was completed. There was gas produced again when the temperature rose above 180° C., and it was observed that a liquid was produced from the greasy substance. The produced liquid was collected at a high efficiency under the depressurized condition.

While collecting the liquid under the depressurized condition, the flask continued to be heated. As a result, the collected fraction was 53.2 g; the purity of the corresponding fluorinated vinyl ether was 92.7%; and hydrogen fluoride adduct was 0.77%. The residuals were homologs with smaller numbers of HFPO and a small amount of the raw materials that had not reacted. The resulted substances were analyzed by gas chromatography with columns of both SE-30 and UCON OIL. The substances that had not reacted were quantitatively analyzed by comparison with the analysis data for the products added with methanol. (The same for the embodiments below.)

Embodiment 2

930 g of potassium carbonate anhydride and then 2713 g of HFPO, were quickly put into a lateral-type biaxial stirring reaction tank (kneader) with a content volume of 5 l having a pressure meter; a header with an opening to discharge nitrogen, vacuum or gases; and a jacket where the heater can heat a heat medium.

The materials were heated and maintained at 130° C. in the tank while being stirred, and gas produced was collected. The volume of the collected gas was about 100 l. It was confirmed through the infrared absorption that the gas was carbonic acid gas with a very small amount of acid fluorides.

After that gas production was completed in about 2 hours, the materials were heated up to 200° C. while the pressure was reduced and maintained at 100 mmHg. 38 g of fraction collected then was considered to be the initial fraction. Then the temperature was raised and maintained at 230° C. to thermally decompose the tank content. While the thermal decomposition was steadily progressing, fractions were collected at a certain rate. The fractions collected were the main fractions 1, 2 and 3. Their amounts were 562 g, 850 g and 714 g respectively. The analysis result of them are as follows: (Numerals in the table are represented by %. The same for the data provided below.)

| Fraction | Main fraction 1 | Main fraction 2 | Main fraction 3 |
| --- | --- | --- | --- |
| Substance not reacted | 4.9 | — | — |
| Objective substance | 82.8 | 97.0 | 97.6 |
| Hydrogen fluoride adduct | 12.1 | 2.3 | 1.6 |
| Lower molecular weight substance etc. | 0.2 | 0.7 | 0.8 |

The reaction residuals collected were 799 g of gray granular and powder solid substance.

Embodiment 3

579.6 g of potassium carbonate anhydride and 2591.6 g of $HFPO_3$ were quickly put into a tank as in the embodiment 2. After the materials were reacted as in the embodiment 2 at 130° C. for 2 hours, 82.4 g of the initial fraction was collected at 200° C. under the depressurized condition. The materials were further heated up to 230° C. while the pressure was maintained at reduced 20 mmHg. Under those conditions, vapor produced was collected in the bath of dry ice/methanol. The collected fractions were the main fractions 1 and 2. The analysis result of them are as follows:

| Fraction | Initial fraction | Main fraction 1 | Main fraction 2 |
| --- | --- | --- | --- |
| Amount | 82.4 g | 1765 g | 1016 g |
| Substance not reacted | — | — | — |
| Objective substance | — | 83.8 | 97.2 |
| Hydrogen fluoride adduct | — | 15.1 | 2.8 |
| Lower molecular weight substance etc. | — | 1.1 | 1.0 |

The amount of the reaction residuals collected were 547 g.

Embodiment 4

A dropping tube for acid fluoride was attached to the reaction tank header; a dry-ice reflux cooling device to the discharge outlet; and it was made possible to seal the sealing part of the stirring axes of the tank with nitrogen gas. Then, as in the embodiment 2, 579.6 g of potassium carbonate anhydride was put into the tank, and the material was heated at 200° C. for 1 hour, being permeated with nitrogen gas. Then, after the tank content was cooled down to 100° C., 2591.4 g of HFPO$_2$ was dropped through the dropping tube. After the dropping was finished, its temperature was raised to 130° C. and the reaction was continued for 2 hours. After the reaction, the temperature was raised, the pressure reduced, and the fractions were collected, as in the embodiment 2. The analysis data for the resulted substance were as follows.

| Fraction | Initial fraction | Main fraction 1 | Main fraction 2 | Main fraction 3 |
|---|---|---|---|---|
| Amount | 177.3 g | 779.5 g | 793.2 g | 464.7 g |
| Substance not reacted | — | — | — | — |
| Objective substance | 75.2 | 95.4 | 99.8 | 98.7 |
| Hydrogen fluoride adduct | 24.6 | 4.4 | Trace | Trace |
| Lower molecular weight substance etc. | 0.2 | 0.2 | 0.2 | 1.3 |

The amount of the reaction residuals collected were 569.7 g.

Embodiment 5

As in the embodiment 4, 560 g of potassium carbonate anhydride was put into the tank, and the material was heated at 200° C. for 2 hour, being permeated with nitrogen gas. Then, after the tank content was cooled down to 130° C., 2670 g of HFPO$_2$ was dropped through the dropping tube over a period of 3 hours. Gas produced in the reaction was released through the reflux cooling tube cooled with dry ice. After the reaction, the temperature was raised, the pressure reduced, and the fractions were collected, as in the embodiment 4. The analysis data for the resulted substance were as follows.

| Fraction | Initial fraction | Main fraction |
|---|---|---|
| Amount | 177 g | 2038.5 g |
| Substance not reacted | — | — |
| Objective substance | 96.35 | 99.27 |
| Hydrogen fluoride adduct | 2.40 | 0.54 |
| Lower molecular weight substance etc. | 1.25 | 0.19 |

Comparative Example 1

30 g of potassium carbonate anhydride was filled into a glass reaction tube 2.4 cm diameter and 30 cm long. Then, the tube was heated up to 250° C. with a heater coiled around it while nitrogen gas was passed through it to dry the substance. A flask with a content volume of 100 ml was placed under the tube and it was heated at 200° C. 100 g of HFPO$_2$ was dropped little by little in the flask and evaporated to pass HFPO$_2$ gas through the tube with nitrogen gas being flown. The gas coming out of the tube was collected with dry ice/methanol. The amounts of the obtained fraction and the collected liquid, and the composition are as follows:

| Fraction | 1 | 2 |
|---|---|---|
| Amount collected | 38.5 g | 27.4 g |
| Substance not reacted | 0.3 | 28.3 |
| Objective substance | 87.1 | 66.9 |
| Hydrogen fluoride adduct | 0.5 | 0.1 |
| Lower molecular weight substance etc. | 12.1 | 4.7 |

Comparative example 2

220 g of HFPO$_2$ was made into methyl ester by adding methanol. Water was removed from the methyl ester through a single distillation, and the substance was saponified with NaOH dissolved in methanol. After the substance was heated to distill out the methanol, the viscous liquid was placed on a stainless plate and dried at a temperature of 100° C. After the substance was put into a separable flask, it was heated to collect fraction. The amount of the fraction collected was 146.2 g. The composition of the substance was as follows:

| Fraction | |
|---|---|
| Amount collected | 146.2 g |
| Substance not reacted | — |
| Objective substance | 92.3 |
| Hydrogen fluoride adduct | 6.8 |
| Lower molecular weight substance etc. | 0.9 |

Reference example 1

44.9 g of fraction was collected in the same process as the embodiment 1 except that the amount of potassium carbonate anhydride used was 6 g. The composition of the resulted substances was as follows:

| | |
|---|---|
| Substance not reacted | 58.7 |
| Objective substance plus hydrogen fluoride adduct | 41.1 |
| Lower molecular weight substance etc. | 0.2 |

Embodiment 6

The process of the embodiment 5 was repeated except that the amount of potassium carbonate anhydride was 1020 g and that of HFPO$_2$ was 1960 g. Then, the same amount of HFPO$_2$ was further reacted with the produced substances. The results were as follows:

| Fraction | Initial fraction 1 | Main fraction 1 | Initial fraction 2 | Main fraction 2 |
|---|---|---|---|---|
| Amount | 183 g | 1372 g | 161 g | 1764 g |
| Substance not reacted | — | — | — | — |
| Objective substance | 94.71 | 98.31 | 97.29 | 99.07 |
| Hydrogen fluoride adduct | 4.40 | 0.93 | 1.73 | 0.49 |
| Lower molecular weight substance etc. | 0.89 | 0.76 | 0.98 | 0.44 |

We claim:

1. A method for preparing a fluorinated vinyl ether of the formula Rf—O—CF=CF$_2$, wherein Rf is Rf'—1 or Rf'—

$(OCXYCF_2CF_2)_m$—; X and Y are fluorine, chlorine, bromine or iodine; l is 1 to 4; m is 1 to 4; Rf is a $C_1$–$C_4$ perfluoroalkyl group or $CX'Y'Z'(CF_2)_n$— wherein X' and Y' are hydrogen, fluorine, chlorine or bromine; Z' is hydrogen, fluorine, chlorine, bromine or iodine; and n is 0 to 4; which comprises:

first reacting an acid halide of the formula Rf—O—CF($CF_2$X)COY with an alkali or alkaline earth metal carbonate or sulfate, or a metal oxide, in the absence of a solvent, to form a metal salt of a fluorinated carboxylic acid of the formula Rf—O—CF($CF_2$X)COOH; said reaction being affected at 50 to 200° C. and at a temperature below the decomposition temperature of the metal salt;

removing volatile impurities and unreacted reactants from the metal salt by distillation; and then heating the metal salt to 180 to 280° C. and at a temperature above the decomposition temperature of the metal salt to produce the fluorinated vinyl ether.

2. A method according to claim 1, wherein the acid halide is purified by distillation.

3. A method according to claim 1, wherein the alkali or alkaline earth metal carbonate or sulfate, or the metal oxide, is dehydrated by heating.

4. A method according to claim 1, wherein a stoichiometric excess of the metal carbonate, sulfide or oxide is used relative to the acid halide.

* * * * *